United States Patent

Machida et al.

[11] Patent Number: 5,017,698
[45] Date of Patent: May 21, 1991

[54] SPIROOXAZINE PHOTOCHROMIC COMPOUNDS

[75] Inventors: Katsuichi Machida, Hino; Akira Saito, Matsudo; Teruo Sakagami, Nerima, all of Japan

[73] Assignee: Kureha Kagaku Kogyo Kabushiki Kaisha, Tokyo, Japan

[21] Appl. No.: 357,220

[22] Filed: May 26, 1989

[30] Foreign Application Priority Data

Jul. 5, 1988 [JP] Japan .................. 63-165877

[51] Int. Cl.$^5$ .......................... C07D 498/20
[52] U.S. Cl. .................................. 544/71
[58] Field of Search .......................... 544/71

[56] References Cited

U.S. PATENT DOCUMENTS

| 4,634,767 | 1/1987 | Hoelscher et al. ............... 544/71 |
| 4,637,698 | 1/1987 | Kwak et al. ................. 544/71 X |
| 4,719,296 | 1/1988 | Irie et al. .................... 544/71 |

FOREIGN PATENT DOCUMENTS

| 1927849 | 12/1970 | Fed. Rep. of Germany . |
| 28892 | 9/1970 | Japan . |
| 48631 | 12/1974 | Japan . |
| 36284 | 3/1980 | Japan . |
| 53586 | 3/1985 | Japan . |
| 112880 | 6/1985 | Japan . |
| 53288 | 3/1986 | Japan . |
| 263982 | 11/1986 | Japan . |
| 3303984 | 12/1988 | Japan . |

OTHER PUBLICATIONS

Publication No. WO 87/00524 (Optische Werke G. Rodenstock), 1-1987.

Primary Examiner—Richard L. Raymond
Attorney, Agent, or Firm—Oliff & Berridge

[57] ABSTRACT

Disclosed herein is a photochromic compound comprising a spirooxazine compound represented by the following general formula (I):

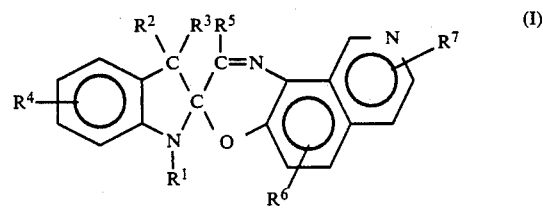

wherein $R^1$ means an alkyl, allyl or alkoxyalkyl group, or a substituted or unsubstituted aralkyl or aryloxyalkyl group, $R^2$ and $R^3$ individually denote a substituted or unsubstituted alkyl group, $R^4$, $R^5$, $R^6$ and $R^7$ stand individually for a hydrogen or halogen atom, or an alkyl, alkoxy, hydroxy, alkoxyalkyl, or substituted or unsubstituted amino group. A photochromic composition comprising the photochromic compound and a phenol derivative, fluorine-containing alcohol or hindered amine type light stabilizer is also disclosed.

4 Claims, No Drawings

SPIROOXAZINE PHOTOCHROMIC COMPOUNDS

BACKGROUND OF THE INVENTION (1) Field of the Invention:

This invention relates to a novel photochromic compound and to a photochromic composition, which comprises the photochromic compound, useful as a variety of recording materials or photochromic materials.

(2) Description of the Related Art:

A variety of photochromic organic compounds have heretofore been known. Of these, spirooxazine compounds are known as those having relatively good repeatability of color-developing function, namely, durability of the color-developing function. 1,3,3-Trimethylspiro[indoline-2,3'-(3H)-naphtho(2,1-b)(1,4)oxazine] and derivatives thereof are disclosed in, for example, Japanese Patent Publication No. 28892/1970, Japanese Patent Publication No. 48631/1974, Japanese Patent Laid-Open No. 36284/1980, Japenese Patent Laid-Open No. 53586/1985, Japanese Patent Laid-Open No. 53288/1986 and Japanese Patent Laid-Open No. 263982/1981.

Photochromic compounds consisting of the conventional respective spirooxazine compounds however involve a problem that they do not exhibit enough photochromism at room temperature or above room temperature.

SUMMARY OF THE INVENTION

An object of this invention is to provide a photochromic compound, which solves the above-mentioned problem and exhibits excellent photochromism even at room temperature or above room temperature.

Another object of this invention is to provide a photochromic composition comprising the photochromic compound which exhibits still enhanced photochromism.

In an aspect of this invention, there is thus provided a photochromic compound comprising a spirooxazine compound represented by the following general formula (I):

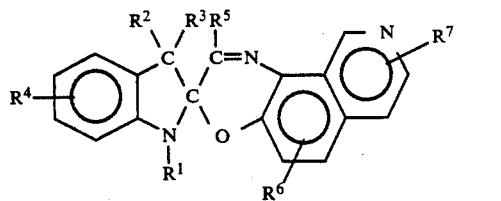

wherein $R^1$ means an alkyl, allyl or alkoxyalkyl group, or a substituted or unsubstituted aralkyl or aryloxyalkyl group, $R^2$ and $R^3$ individually denote a substituted or unsubstituted alkyl group, $R^4$, $R^5$, $R^6$ and $R^7$ stand individually for a hydrogen or halogen atom, or an alkyl, alkoxy, hydroxy, alkoxyalkyl, or substituted or unsubstituted amino group.

In another aspect of this invention, there is also provided a photochromic composition comprising the photochromic compound consisting of the spirooxazine compound represented by the general formula (I) and a phenol derivative, fluorine-containing alcohol and/or hindered amine type light stabilizer as colored state enhancer.

DETAILED DESCRIPTION OF THE INVENTION AND PREFERRED EMBODIMENTS

According to this invention, the spirooxazine compounds represented by the general formula (I) are provided as photochromic compounds. As specific examples of these spirooxazine compounds, may be mentioned:

1,3,3-trimethylspiro[indoline-2,3'-(3'-(3H)-pyrido(3,4-f)(1,4)benzooxazine];

1-isopropyl-3,3-dimethylspiro[indoline-2,3'-(3H)-prido(3,4-f)(1,4)benzooxazine];

1-benzyl-3,3-dimethylspiro[indoline-2,3'-(3H)(-pyrido(3,4-f)(1,4)benzooxazine];

1-(2-phenoxyethyl)-3,3-dimethylspiro[indoline-2,3'-(3H)-pyrido(3,4-f)(1,4)benzooxazine];

1-(p-methoxybenzyl)-3,3-dimethylspiro[indoline-2,3'-(3H)-pyrido(3,4-f)(1,4)benzooxazine];

1-(2-methoxyethyl)-3,3-dimethylspiro[indoline-2,3'-(3H)-pyrido(3,4-f)(1,4)benzooxazine];

1,3-dimethyl-3-ethylspiro[indoline-2,3'-(3H)-pyrido(3,4-f)(1,4)benzooxazine];

5-chloro-1,3,3-trimethylspiro[indoline-2,3'-(3H)-pyrido(3,4-f)(1,4)benzooxazine];

1,3,3,5-tetramethylspiro[indoline-2,3'-(3H)-pyrido(3,4-f)(1,4)benzooxazine];

2'-(N,N-diethylamino)-1,3,3-trimethylspiro[indoline-2,3'-(3H)-pyrido(3,4-f)(1,4benzooxazine];

1-isopropyl-3-methyl-3-ethylspiro[indoline-2,3'-(3H)-pyrido(3,4-f)(1,4)benzooxazine ;

1-phenethyl-3,3-dimethylspiro[indoline-2,3'-(3H)-pyrido(3,4-f)(1,4)benzooxazine];

1-(ethoxyethyl)-3,3-dimethylspiro[indoline-2,3'-(3H)-pyrido(3,4-f)(1,4)benzooxazine];

5-chloro-1,3-dimethyl-3-ethylspiro]indoline-2,3'-(3H)-pyrido(3,4-f)(1,4)benzooxazine];

5-methoxy-1,3,3-trimethylspiro[indoline-2,3'-(3H)-pyrido(3,41,4)benzooxazine];

1,3,3,5,6-pentamethylspiro[indoline-2,3'-(3H)-pyrido(3,4-f)(1,4)benzooxazine];

8'-hydroxy-1,3,3-trimethylspiro[indoline-2,3'-(3H)-pyrido(3,4-f)(1,4)benzooxazine]; and 8'-methoxy-1,3,3-trimethylspiro[indoline-2,3'-(3H)-pyrido(3,4-f)(1,4)benzooxazine].

Needless to say, the spirooxazine compounds according to this invention are not limited to these compounds.

Among the spirooxazine compounds represented by the general formula (I), compounds, wherein $R^1$ is a linear or branched alkyl group having 4–25 carbon atoms, have excellent weathering resistance and color-developing properties. As specific examples of these spirooxazine compounds, may be mentioned:

1-(n-butyl)-3,3-dimethylspiro[indoline-2,3'-(3H)-pyrido(3,4-f)(1,4)benzooxazine];

1-isobutyl-3,3-dimethylspiro[indoline-2,3'-(3H)-pyrido(3,4-f)(1,4)benzooxazine];

1(n-pentyl)-3,3-dimethylspiro[indoline-2,3'-(3H)-pyrido(3,4-f)(1,4)benzooxazine];

1-isoamyl-3,3-dimethylspiro[indoline-2,3'-(3H)-pyrido(3,4-f)(1,4)benzooxazine];

1-(n-hexyl)-3,3-dimethylspiro[indoline-2,3'-(3H)-pyrido(3,4-f)(1,4)benzooxazine];

1-(n-heptyl)-3,3-dimethylspiro[indoline-2,3'-(3H)-pyrido(3,4-f)(1,4)benzooxazine];

1-(n-hexyl)-3-methyl-3-ethylspiro[indoline-2,3'-(3H)-pyrido(3,4-f)(1,4)benzooxazine];

1-cyclohexyl-3,3-dimethylspiro[indoline-2,3'-(3H)-pyrido(3,4-f)(1,4)benzooxazine];

1-cyclohexylmethyl-3,3-dimethylspiro[indoline-2,3'-(3H)-pyrido(3,4-f)(1,4)benzooxazine];

1-(n-octyl)-3,3,5-trimethylspiro[indoline-2,3'-(3H)-pyrido(3,4-f)(1,4)benzooxazine];

1-(2-ethylhexyl)-3,3-dimethylspiro[indoline-2,3'-(3H)-pyrido(3,4-f)(1,4)benzooxazine];

1-(n-decyl)-3,3-dimethylspiro[indoline-2,3'-(3H)-pyrido(3,4-f)(1,4)benzooxazine];

1-(n-dodecyl)-3,3,2'-trimethylspiro[indoline-2,3'-(3H)-pyrido(3,4-f)(1,4)benzooxazine];

1-(n-dodecyl)-3-methyl-3-ethylspiro[indoline-2,3'-(3H)-pyrido(3,4-f)(1,4)benzooxazine];

1-(n-dodecyl)-3,3-dimethylspiro[indoline-2,3'-(3H)-pyrido(3,4-f)(1,4)benzooxazine];

1-(n-octadecyl)-3,3-dimethylspiro[indoline-2,3'-(3H)-pyrido(3,4-f)(1,4)benzooxazine];

1-(n-docosyl)-3,3-dimethylspiro[indoline-2,3'-(3H)-pyrido(3,4-f)(1,4)benzooxazine];

1-(n-hexyl)-3,3,4,5-tetramethylspiro[indoline-2,3'-(3H)-pyrido(3,4-f)(1,4)benzooxazine];

1-(n-hexyl)-3,3,5,6-tetramethylspiro[indoline-2,3'-(3H)-pyrido(3,4-f)(1,4)benzooxazine];

8'-hydroxy-1-(n-hexyl)-3,3-dimethylspiro[indoline-2,3'-pyrido(3,4-f)(1,4) benzooxazine]; and others.

The above-mentioned spirooxazine compounds are separately synthesized, for example, by reacting an 8-nitroso-7-isoquinolinol derivative with an indoline derivative containing one or more of intended substituent groups. Specifically, the reaction may be conducted by dissolving both isoquinolinol derivative and indoline derivative in a suitable solvent such as ethyl alcohol or toluene and then refluxing the resultant solution in an inert gas atmosphere. An indolinium salt having the intended substituent groups may also be used in place of the above indoline derivative. As described in Japanese Patent Laid-Open No. 18783/1986 and Japanese Patent Laid-Open No. 165388/1986, it is also alternatively possible to synthesize an indolinium salt and then to react the resultant indolinium salt with a 8-nitroso-7-isoquinolinol derivative without isolating and purifying the indolinium salt. In these reactions, it is also allowed to add, as a catalyst, a base such as triethylamine. The spirooxazine compounds thus synthesized may be purified by a technique such as a recrystallization, column separation or active carbon treatment method, if necessary.

The photochromic composition according to this invention is composed of the above-described photochromic compound and a phenol derivative or fluorine-containing alcohol. In this case, the addition of the phenol compound or fluorine-containing alcohol to the above photochromic compound makes its colored state more stable and so makes the photochromic compound exhibit much deeper colored state.

As specific examples of the phenol derivative useful in the practice of this invention, may be mentioned alkyl-substituted phenols such as p-tert-butylphenol, 2,4-di-tert-butyl-6-methylphenol; diphenols such as bisphenol A and derivatives thereof, and m,m'-dihydroxybiphenyl; and the like. A phenol resin may be used preferably. Of these, bisphenol A and derivatives thereof are particularly preferred.

As specific examples of the fluorine-containing alcohol, may be mentioned 2,2,2-trifluoroethyl alcohol, 2,2,3,3-tetrafluoro-1-propyl alcohol, 2,2,3,4,4,4-hexafluoro-1-butyl alcohol, 1,1,1,3,3,3-hexafluoro-2-propyl alcohol, 2-(n-perfluorohexyl)ethyl alcohol, 2-(n-perfluorooctyl)ethyl alcohol, pentafluorphenol, 2,2-bis(4-hydroxyphenyl)hexafluoropropane, etc. Of these fluorine-containing alcohols, 1,1,1,3,3,3-hexafluoro-2-propyl alcohol is particularly preferred.

The photochromic compound or photochromic composition according to this invention is embodied as products having photochromic function by causing it to contain in solid media.

Here, no particular limitation is imposed on the solid media so long as the photochromic compound may be contained either singly or in combination with the phenol derivative or fluorine-containing alcohol therein. Therefore, they may be mere binders or resins, which constitute products having their inherent function by themselves, for example, resins constituting optical materials.

As specific examples of such resins, may be mentioned polyol(allyl carbonates), acrylic resins, cellulose resins, polyvinyl alcohol, polyvinyl acetate, urethane resins, epoxy resins, silicone resins, polystyrene, polyesters such as polyethylene terephthalate, polyvinyl butyral, polyamides, polyvinyl chloride, polyvinylidene chloride, etc.

No particular limitation is imposed on the proportion of the spirooxazine compound in the solid medium composed of such a resin. It is used in a range of 0.001–100 parts by weight, preferably, 0.01–50 parts by weight per 100 parts by weight of the solid medium. The phenol derivative or fluorine-containing alcohol is used in a range of 0.1–100 parts by weight, preferably, 0.5–50 parts by weight per 100 parts by weight of the solid medium. However, the range does not apply to the case where a phenol resin is used as the solid medium.

The photochromic compounds and photochromic compositions of this invention can be utilized in the same manner as in the conventional photochromic materials. Accordingly, they can be put to practical use by using, for example, the following methods:

(1) A method in which a mixture obtained by blending the above photochromic compound or photochromic composition with a binder is provided as a raw material, and the mixture is then formed into a film, plate or other desired shape by a method such as casting or melt forming.

According to this method, solid products having photochromic function by themselves can be made.

(2) A method in which a solution obtained by dissolving the above photochromic compound or photochromic composition along with a binder in a suitable common solvent is provided as a coating formulation, the coating formulation is applied on substrates made of various kinds of optical materials and the solvent is then removed, thereby forming respective photochromic layers on the substrates.

According to this method, optical materials such as a lens having a photochromic layer can be produced.

(3) A method in which the solution in the above method (2) is cast.

According to this method, photochromic films can suitably be formed.

(4) A method in which an appropriate dispersing medium is used in place of the solvent in the above method (2) or (3), the above photochromic compound or photochromic composition is dispersed along with a binder in the dispersing medium, and the resulting dispersion is then used.

(5) A method in which a polymerizable monomer, which forms a binder by its polymerization, is used instead of a portion or the whole of the binder in the above method (1), (2), (3) or (4) so that a formed photochromic product, layer, film or the like is subjected further to a polymerization treatment.

According to this method, products, layers, films, etc., which have photochromic function and are composed of a polymer, can be obtained. Accordingly, optical materials such as lens, which have photochromic function can be directly produced, for example, by adding the photochromic compound or composition to a monomer composition, which provides an optical material by its polymerization, and then charging the resultant mixture in a mold for cast polymerization, whereby the monomer composition is subjected to a polymerization treatment. In this case, it is preferable to use the fluorine-containing alcohol in that the alcohol is unlikely to hinder a polymerization reaction as in the phenol derivative, and an intended photochromic polymer can hence be obtained satisfactorily.

Upon practice of the methods described above, one or more of suitable additives such as antioxidants, ultraviolet absorbents, light stabilizers and the like may also be added.

The weathering resistance of the resulting photochromic optical material can be improved by using, particularly, a hindered amine type light stabilizer as a light stabilizer. As such a light stabilizer, may be effectively used a commercially-available product such as:
bis(1,2,2,6,6-pentamethyl-4-piperidyl) sebacate;
bis(2,2,6,6-tetramethyl-4-piperidyl) sebacate;
di(1,2,2,6,6-pentamethyl-4-piperidyl)butyl(3',5'-di-tert-butyl-4-hydroxybenzyl)malonate;
1-{2-[3-(3,5-di-tert-butyl-4-hydroxyphenyl)propionyloxy]ethyl}-4-[3-(3,5-di-tert-butyl-4-hydroxyphenyl)propionyloxy]-2,2,6,6-tetramethylpiperidine;
poly{[6-((1,1,3,3-tetramethylbutyl)amino)-1,3,5-triazine-2,4-di-yl][1,6-(2,2,6,6-tetramethyl-4-piperidyl)aminohexamethylene]};
poly{[6-((morpholino)-S-triazine-2,4-di-yl][1,6-(2,2,6,6-tetramethyl-4-piperidyl)aminohexamethylene]}; or
a polymer of dimethyl succinate with 4-hydroxy-2,2,6,6-tetramethyl-1-piperidinethanol.

The light stabilizer is used in an amount of 0.01-50 parts by weight, preferably, 0.01-30 parts by weight per 100 parts by weight of the solid medium.

Furthermore, the addition of a singlet oxygen quencher is effective in restraining an adverse effect on the color-developing mechanism of the spirooxazine compound due to oxygen, thereby enhancing the repeated durability of its color-developing function.

As specific examples of such a singlet oxygen quencher, may be mentioned β-carotene, various Ni(II) complexes of Schiff bases, 1,4-diazabicyclo[2,2,2]octane, amines such as triethylamine and the phenols described above, etc. Of these, the amines and phenols may preferably be used because they have no absorption at the visible region though their singlet oxygen quenching coefficients are somewhat small. It is more desirable to add the singlet oxygen quencher in a greater amount. The quencher is used in an amount of 0.1-100 parts by weight, preferably, 0.5-50 parts by weight per 100 parts by weight of the solid medium.

Since the photochromic compound of this invention consists of the spirooxazine compound having a particular chemical structure, it is good in durability of excellent colored state owing to its specificity and exhibits excellent color-developing function at room temperatures or above room temperature as will be apparent from the description of the following Examples. In addition, the photochromic composition according to this invention allows the spirooxazine compound to intensify the degree of its color development owing to the phenol derivative or fluorine-containing alcohol contained together in the composition. As a result, its color density becomes still higher and besides, its colored state is kept much more stable.

Therefore, the photochromic compounds and photochromic compositions of this invention can suitably be used as optical materials for optical instruments such as various displays, memorise, photochromic lenses, photochromic filters and actinometers, and the like by improving their characteristics and/or properties as described above.

EXAMPLES

The present invention will hereinafter be described by the following Examples. It should however be borne in mind that the present invention is not necessarily limited to or by the following Examples.

Incidentally, the measurement of light transmittance in the following Examples and Comparative Examples is conducted as to light of a wavelength at which the light transmittance varies to the greatest extent.

EXAMPLE 1

Synthesis Example

Synthesis of
1,3,3-trimethylspiro[indoline-2,3'-(3H)-pyrido(3,4-f)(1,4)benzooxazine]

In 60 ml of ethyl alcohol, were dissolved 5.72 g of 1,3,3-trimethyl-2-methyleneindoline and 5.22 g of 8-nitroso-7-isoquinolinol. The resultant solution was refluxed and reacted for 2 hours in a nitrogen gas atmosphere.

After the reaction, the solvent ethyl alcohol was concentrated, and the concentrate was subjected to a separation treatment by a column chromatography making use of silica gel and chloroform as a solid support and developing solvent. After the developing solvent was distilled off, the resultant solid matter was purified by recrystallization from a mixed solvent of acetone and hexane to obtain 0.7 g of pale yellow powder.

This compound was identified as 1,3,3-trimethylspiro[indoline-2,3'-(3H)-pyrido(3,4-f)(1,4)benzooxazine] by nuclear magnetic resonance (NMR) spectra, infrared absorption spectra and CHN elemental analysis.

A result of the elemental analysis was as follows:
C: 76.51 wt. %, H: 6.02 wt. %, N: 12.51 wt. %.
These values almost corresponded to the following calculated values:
C: 76.57 wt. %, H: 5.81 wt. %, N: 12.76 wt. %.
On the other hand, NMR spectra of the compound were found to be 1.4 ppm (6H), 2.8 ppm (3H), 6.6–10.0 ppm (10H) in deuteriochloroform.

Application Example

In 100 parts by weight of methyl ethyl ketone, 4.0 parts by weight of 1,3,3-trimethylspiro[indoline-2,3'-(3H)-pyrido(3,4-f)(1,4)benzooxazine] were dissolved along with 60 parts by weight of an epoxy resin precursor, "EPONIX #1100 CLEAR" (trade name; product of Dai Nippon Toryo Co., Ltd.) to obtain a coating formulation.

The coating formulation was applied by the dipping technique on the surface of a slide glass. Methyl ethyl ketone was evaporated at 40° C. until the coated surface became tack-free. Thereafter, the coating formulation was hardened at 80° C. for 16 hours, thereby forming a photochromic film of 10 μm thick.

The thus-formed film was somewhat greenish. When the film was exposed to ultraviolet light, it developed a color. Its light transmittance at room temperature at the wavelength of 612 nm was widely lowered from 82% before the exposure of the ultraviolet light to 44% upon the 5 minutes exposure of the ultraviolet light. When it was placed in a dark place thereafter, the light transmittance returned to its original state.

Comparative Example 1

A photochromic film having a thickness of 10 μm was formed in exactly the same manner as in Example 1 except that 4.0 parts by weight of 1,3,3-trimethylspiro-[indoline-2,3'-(3H)-naphtho(2,1-b)(1,4) oxazine ] were used instead of 4.0 parts by weight of 1,3,3-trimethyl-spiro[indoline-2,3'-(3H)-pyrido(3,4-f)(1,4)benzooxazine].

When the thus-formed film was exposed to ultraviolet light, it developed a color. The variations of its light transmittance at room temperature at the wavelength of 610 nm were however confined to reducing from 92% before the exposure of the ultraviolet light to 78% upon the 5 minutes exposure of the ultraviolet light.

Exmaple 2

In 100 parts by weight of methyl ethyl ketone, 4.0 parts by weight of 1,3,3-trimethylspiro[indoline-2, 3'-(3H) -pyrido(3, 4-f)(1, 4)benzooxazine] and 10.0 parts by weight of bisphenol A were dissolved along with 60 parts by weight of an epoxy resin precursor, "EPONIX #1100 CLEAR" (trade name; product of Dai Nippon Toryo Co., Ltd.) to obtain a coating formulation.

The coating formulation was applied by the dipping technique on the surface of a slide glass. Methyl ethyl ketone was evaporated at 40° C. until the coated surface became tack-free. Thereafter, the coating formulation was hardened at 80° C. for 16 hours, thereby forming a photochromic film of 10 μm thick.

The thus-formed film was somewhat greenish. When it was exposed to ultraviolet light, it developed a color. Its light transmittance at room temperature at the wavelength of 612 nm was widely lowered from 76% before the exposure of the ultraviolet light to 30% upon the 5 minutes exposure of the ultraviolet light. When it was placed in a dark place thereafter, the light transmittance returned to its original state.

EXAMPLE 3

Synthesis Example

Synthesis of 1-(p-methoxybenzyl)-3,3-dimethylspiro[indoline-2,3'-(3H)-pyrido(3,4-f)(1,4)-benzooxazine]

Dissolved in 100 ml of ethyl alcohol were 7.65 g of 1-(p-methoxybenzyl)-2,3,3-trimethylindolinium bromide, 3.48 g of 8-nitroso-7-isoquinolinol and 5 g of triethylamine. The resultant solution was refluxed and reacted for 2 hours in a nitrogen gas atmosphere.

After the reaction, the solvent ethyl alcohol was concentrated, and the precipitated yellowish brown crystals were separated and washed with a small amount of ethyl alcohol. The thus-obtained powder was purified by recrystallization from ethyl alcohol to obtain 0.87 g of pale yellow powder.

This compound was identified as 1-(p-methoxybenzyl)-3,3-dimethylspiro [indoline-2,3'-(3H)-prido-(3,4-f)(1,4)benzooxizine] by NMR spectra, infrared absorption spectra and CHN elemental analysis.

A result of the elemental analysis was as follows:
C: 77.20 wt. %, H: 5.95 wt. %, N: 9.53 wt. %.
These values almost corresponded to the following calculated values:
C: 77.22 wt. %, H: 5.79 wt. %, N: 9.65 wt. %.
On the other hand, NMR spectra of the compound were found to be 1.4 ppm (6H), 3.7 ppm (3H), 4.3 ppm (2H), 6.4–9.9 ppm (14H) in deuteriochloroform.

Application Example

In 100 parts by weight of methyl ethyl ketone, 3.0 parts by weight of 1-(p-methoxbenzyl)-3,3-dimethyl-spiro[indoline-2,3'-(3H)-pyrido(3,4-f)(1,4)benzooxazine] and 10 parts by weight of 1,1,1,3,3,3-hexafluro-2-propyl alcohol were dissolved along with 60 parts by weight of an epoxy resin precursor, "EPONIX #1100 CLEAR" (trade name; product of Dai Nippon Toryo Co., Ltd.), thereby obtaining a coating formulation.

The coating formulation was applied by the dipping technique on the surface of a slide glass. Methyl ethyl ketone was evaporated at 40° C. until the coated surface became tack-free. Thereafter, the coating formulation was hardened at 80° C. for 16 hours, thereby forming a photochromic film of 10 μm thick.

The thus-formed film was somewhat greenish. When the film was exposed to ultraviolet light, it developed a color. Its light transmittance at room temperature at the wavelength of 615 nm was widely lowered from 78% before the exposure of the ultraviolet light to 34% upon the 5 minutes exposure of the ultraviolet light. When it was placed in a dark place thereafter, the light transmittance returned to its original state.

EXAMPLE 4

Synthesis Example

Synthesis of 1,3-dimethyl-3-ethylspiro[indoline-2,3'-(3H)-pyrido(3,4-f)(1,4)benzooxazine]

Dissolved in 100 ml of ethyl alcohol were 15.76 g of 1,2,3-trimetyl-3-ethylindolinium iodide, 8.71 g of 8-nitroso-7-isoquinolinol and 12 g of triethylamine, followed by reflux and reaction of the resultant solution for 2 hours in a nitrogen gas atmosphere.

After the reaction, the solvent ethyl alcohol was concentrated, and the concentrate was separated by a column chromatography making use of silica gel and chloroform as a solid support and developing solvent. The developing solvent was then replaced with a 1:10 mixed solvent of ethyl acetate and hexane so as to conduct again the purification by the column chromatography. After the developing solvent was distilled off, the resultant solid matter was purified by recrystallization from a mixed solvent of acetone and hexane to obtain 0.82 g of pale yellow powder.

This compound was identified as 1,3-dimethyl-3-ethylspiro[indoline-2,3'-(3H)-pyrido(3,4-f)(1,4)benzooxazine] by NMR spectra, infrared absorption spectra and CHN elemental analysis.

A result of the elemental analysis was as follows:

C: 76.90 wt. %, H: 6.41 wt. %, N: 12.15 wt. %.
These values almost corresponded to the following calculated values:
C: 76.94 wt. %, H: 6.16 wt. %, N: 12.24 wt. %.
On the other hand, NMR spectra of the compound were found to be 0.4 ppm (3H), 1.3 ppm (3H), 1.8 ppm (2H), 2.8 ppm (3H), 6.6–10.0 ppm (10H) in deuteriochloroform.

Application Example

To 26.97 parts by weight of 2-hydroxyethyl methacrylate, 23.03 parts by weight of isophorone diisocyanate and 50 parts by weight of 2-ethylhexyl methacrylate, were added 5 parts by weight of 2,6-ditert-butyl-p-cresol as an antioxidant and 0.05 part by weight of di-n-butyltin dilaurate as a urethanating catalyst, followed by urethanating reaction at 60° C. for 3 hours.

After 1 part by weight of 1,3-dimethyl-3-ethyl-spiro[indoline-2,3'-(3H)-pyrido(3,4-f)(1,4)benzooxazine] and 10.0 parts by weight of 1,1,1,3,3,3-hexafluoro-2-propyl alcohol were added to and mixed with the thus-obtained urethanated monomer composition, 1 part by weight of tert-butyl peroxypivalate as a polymerization initiator was added to the resultant mixture, thereby obtaining a solution of a monomer composition containing a photochromic composition.

The thus-obtained solution of the monomer composition was poured into a glass-made mold for the production of a lens and then polymerized while raising its polymerization temperature stepwise. The solutionn was heated at 50° C. for 10 hours, at 60° C. for 5 hours, at 80° C. for 2 hours and then at 100° C. for 1 hour, thereby producing a photochromic lens having a central thickness of 1.3 mm.

The thus-produced lens was tinged with bluish green. When the lens was exposed to ultraviolet light, it developed a color. Its light transmittance at room temperature at the wavelength of 605 nm was widely lowered from 72% before the exposure of the ultraviolet light to 16% upon the 5 minutes exposure of the ultraviolet light. When it was placed in a dark place thereafter, the light transmittance returned to its original state.

EXAMPLE 5

Synthesis Example

[Synthesis of 1-n-hexyl-3,3-dimethylspiro[indoline-2,3'-(3H)-pyrido(3,4-f)(1,4)benzooxazine]

In 200 ml of toluene, 7.39 g of 1-n-hexyl-3,3-dimethyl-2-methyleneindoline and 5.22 g of 8-nitroso-7-isoquinolinol were dissolved. The resultant solution was refluxed and reacted for 6 hours in a nitrogen gas atmosphere.

After the reaction, the solution was cooled and insoluble matter was separated by filtration. The filtrate was then concentrated to obtain a viscous liquid having a blackish brown color. The component soluble in hexane was extracted from the thus-obtained liquid. The extractant was concentrated and was purified by recrystallization from a mixed solvent of acetone and hexane to obtain 1.2 g of pale yellow powder.

This compound was identified as 1-n-hexyl-3,3-dimethylspiro[indoline-2,3'-(3H)-pyrido(3,4-f)(1,4)benzooxazine] by NMR spectra, infrared absorption spectra and CHN elemental analysis.

A result of the elemental analysis was as follows:
C: 78.14 wt. %, H: 7.41 wt. %, N: 10.45 wt. %.
These values almost corresponded to the following calculated values:
C: 78.16 wt. %, H: 7.32 wt. %, N: 10.52 wt. %.
On the other hand, NMR spectra of the compound were found to be 0.6–2.0 ppm (17H), 3.2 ppm (2H), 6.5–10.0 ppm (10H) in deuteriochloroform.

Application Example

To 26.97 parts by weight of 2-hydroxyethyl methacrylate, 23.03 parts by weight of isophorone diisocyanate and 50 parts by weight of 2-ethylhexyl methacrylate, were added 5 parts by weight of 2,6-di-tert-butyl-p-cresol as an antioxidant and 0.05 part by weight of di-n-butyltin dilaurate as a urethanating catalyst, followed by urethanating reaction at 60° C. for 3 hours.

After 0.1 part by weight of 1-n-hexyl-3,3-dimethyl-spiro[indoline-2,3'-(3H)-pyrido(3,4-f)(1,4)benzooxazine] was added to and mixed with the thus-obtained urethanated monomer composition, 1 part by weight of tert-butyl peroxypivalate as a polymerization initiator was added to the resultant mixture, thereby obtaining a solution of a monomer composition containing a photochromic composition.

The thus-obtained solution of the monomer composition was poured into a glass-made mold for the production of a lens and then polymerized while raising its polymerization temperature stepwise. The solution was heated at 50° C. for 10 hours, at 60° C. for 5 hours, at 80° C. for 2 hours and then at 100° C. for 1 hour, thereby producing a photochromic lens having a central thickness of 1.3 mm.

The thus-produced lens was tinged with bluish green. When the lens was exposed to ultraviolet light, it developed a color. Its light transmittance at room temperature at the wavelength of 612 nm was widely lowered from 85% before the exposure of the ultraviolet light to 32% upon the 5 minutes exposure of the ultraviolet light. When it was placed in a dark place thereafter, the light transmittance returned to its original state.

The lens was treated further by means of "Atlas Weather-Ometer Ci35 Model" (trade name; manufactured by Atlas Electric Devices Co.) for 120 hours to conduct an accelerated deterioration treatment. The lens was then exposed to ultraviolet light in the same manner as described above so as to measure its light transmittance at the wavelength of 612 nm. The light transmittance was widely lowered from 83% before the exposure of the ultraviolet light to 40% upon the 5 minutes exposure of the ultraviolet light.

EXAMPLE 6

Synthesis Example

Synthesis of 1-isopropyl-3,3-dimethylspiro[indoline-2,3'-(3H)-pyrido(3,4-f)(1,4)-benzooxazine]

Dissolved in 200 ml of toluene were 6.54 g of 1-isopropyl-2,3,3-trimethylindolinium iodide, 3.81 g of 8-nitroso-7-isoquinolinol and 5.0 g of triethylamine. The resultant solution was refluxed and reacted for 8 hours in a nitrogen gas atmosphere.

After the reaction, the solution was cooled and insoluble matter was separated by filtration. The resultant filtrate was then concentrated to obtain a brown viscous liquid. After concentrating the thus-obtained liquid, the concentrate was purified by recrystallization from a mixed solvent of acetone and hexane to obtain 0.95 g of pale yellow powder.

This compound was identified as 1-isopropyl-3,3-dimethylspiro[indoline-2,3'-(3H)-pyrido(3,4-f)(1,4)benzooxazine] by NMR spectra, infrared absorption spectra and CHN elemental analysis.

A result of the elemental analysis was as follows:
C: 77.23 wt. %, H: 6.71 wt. %, N: 11.48 wt. %.
These values almost corresponded to the following calculated values:
C: 77.28 wt. %, H: 6.49 wt. %, N: 11.76 wt. %.
On the other hand, NMR spectra of the compound were found to be 1.2–1.6 ppm (12H), 3.7 ppm (1H), 6.5–10.0 ppm (10H) in deuteriochloroform.

Application Example

A photochromic lens having a central thickness of 1.3 mm was produced in exactly the same manner as in Example 5 except that 0.5 part by weight of 1-isopropyl-3,3-dimethylspiro[indoline-2,3'-(3H)-pyrido(3,4-f)(1,4)-benzooxazine] was used instead of 0.1 part by weight of 1-hexyl-3,3-dimethylspiro-[indoline-2,3'-(3H)-pyrido-(3,4-f)(1,4)benzooxazine].

The thus-produced lens was somewhat greenish. When the lens was exposed to ultraviolet light, it developed a color. Its light transmittance at room temperature at the wavelength of 612 nm was widely lowered from 80% before the exposure of the ultraviolet light to 27% upon the 5 minutes exposure of the ultraviolet light. When it was placed in a dark place thereafter, the light transmittance returned to its original state.

EXAMPLE 7

Synthesis Example

Synthesis of
1-methoxyethyl-3,3-dimethylspiro[indoline-2,3'-(3H)-pyrido(3,4-f)(1,4)-benzooxazine]

Dissolved in 200 ml of toluene were 20.0 g of 1-methoxyethyl-3,3-dimethyl-2-methyleneindoline and 9.58 g of 8-nitroso-7-isoquinolinol. The resultant solution was refluxed and reacted for 6 hours in a nitrogen gas atmosphere.

After the reaction, the solution was cooled and insoluble matter was separated by filtration. The resultant filtrate was then concentrated and subjected to a separation treatment by a column chromatography making use of silica gel and chloroform as a solid support and developing solvent. After the developing solvent was distilled off, the resultant solid matter was purified by recrystallization from a mixed solvent of acetone and hexane to obtain 1.8 g of pale yellow powder.

This compound was identified as 1-methoxyethyl-3,3-dimethylspiro[indoline-2,3'-(3H)-pyrido(3,4-f)(1,4)-benzooxazine] by NMR spectra, infrared absorption spectra and CHN elemental analysis.

A result of the elemental analysis was as follows:
C: 73.90 wt. %, H: 6.42 wt. %, N: 11.11 wt. %.
These values almost corresponded to the following calculated values:
C: 73.97 wt. %, H: 6.21 wt. %, N: 11.25 wt. %.
On the other hand, NMR spectra of the compound were found to be 1.3 ppm (6H), 3.3–3.7 ppm (7H), 6.5–10.0 ppm (10H) in deuteriochloroform.

Application Example

A photochromic film of 10 μm thick was formed in exactly the same manner as in Example 1 except that 4.0 parts by weight of 1-methoxyethyl-3,3-dimethylspiro[indoline-2,3'-(3H)-pyrido(3,4-f)(1,4)benzooxazine] were used instead of 4.0 parts by weight of 1,3,3-trimethylspiro[indoline-2,3'-(3H)-pyrido-(3,4-f)(1,4)-benzooxazine].

The thus-produced film was somewhat greenish. When the film was exposed to ultraviolet light, it developed a color. Its light transmittance at room temperature at the wavelength of 612 nm was widely lowered from 82% before the exposure of the ultraviolet light to 42% upon the 5 minutes exposure of the ultraviolet light. When it was placed in a dark place thereafter, the light transmittance returned to its original state.

EXAMPLE 8

A photochromic lens having a central thickness of 1.3 mm was produced in exactly the same manner as in Example 5 except that 0.03 part by weight of 1,3-dimethyl-3-ethylspiro[indoline-2,3'-(3H)-pyrido(3,4-f)-(1,4)benzooxazine] was used instead of 0.1 part by weight of 1-n-hexyl-3,3-dimethylspiro-[indoline-2,3'-(3H)-pyrido(3,4-f)(1,4)benzooxazine].

The thus-produced lens was somewhat greenish. When the lens was exposed to ultraviolet light, it developed a color. Its light transmittance at room temperature at the wavelength of 605 nm was widely lowered from 92% before the exposure of the ultraviolet light to 55% upon the 5 minutes exposure of the ultraviolet light. When it was placed in a dark place thereafter, the light transmittance returned to its original state.

EXAMPLE 9

A photochromic lens having a central thickness of 1.3 mm was produced in exactly the same manner as in Example 5 except that 0.5 part by weight of bis(2,2,6,6-tetramethyl-4-piperidyl)sebacate ("SANOL LS-770"; trade name; product of Sankyo Company, Limited) of a hindered amine type light stabilizer was added to the solution of the monomer composition in Example 5.

The thus-produced lens was tinged with bluish green. When the lens was exposed to ultraviolet light, it developed a color. Its light transmittance at room temperature at the wavelength of 612 nm was widely lowered from 85% before the exposure of the ultraviolet light to 32% upon the 5 minutes exposure of the ultraviolet light. When it was placed in a dark place thereafter, the light transmittance returned to its original state.

Furthermore, the lens was subjected to an accelerated deterioration treatment in the same manner as in Example 5, and then exposed to ultraviolet light in the same manner as described above so as to measure its light transmittance at the wavelength of 612 nm. The light transmittance was widely lowered from 84% before the exposure of the ultraviolet light to 38% upon the 5 minutes exposure of the ultraviolet light.

EXAMPLE 10

Synthesis Example

Synthesis of
1-n-octadecyl-3,3-dimethylspiro[indoline-2,3'-(3H)-pyrido(3,4-f)(1,4)benzooxazine]

In 250 ml of toluene, 12.35 g of 1-n-octadecyl-3,3-dimethyl-2-methyleneindoline and 5.4 g of 8-nitroso-7-isoquinolinol were dissolved. The resultant solution was refluxed and reacted for 10 hours in a nitrogen gas atmosphere.

After the reaction, the solution was cooled and insoluble matter was separated by filtration. The filtrate was then concentrated, and the resulting viscous liquid of a blackish brown color was subjected to a separation treatment by a column chromatography making use of silica gel and a mixed solvent of hexane and ethyl acetate as a solid support and developing solvent. After the developing solvent was distilled off, the resultant solid matter was purified by recrystallization from a mixed solvent of acetone and hexane to obtain 3.2 g of pale yellow powder.

This compound was identified as 1-n-octadecyl-3,3-dimethylspiro[indoline-2,3'-(3H)-pyrido(3,4-f)(1,4)-benzooxazine] by NMR spectra, infrared absorption spectra and CHN elemental analysis.

A result of the elemental analysis was as follows:
C: 80.28 wt. %, H: 10.12 wt. %, N: 7.21 wt. %.
These values almost corresponded to the following calculated values:
C: 80.37 wt. %, H: 9.41 wt. %, N: 7.40 wt. %.
On the other hand, NMR spectra of the compound were found to be 0.7–1.9 ppm (41H), 3.2 ppm (2H), 6.5–10.0 ppm (10H) in deuteriochloroform.

Application Example

In a mixed solvent of 60 parts by weight of methyl ethyl ketone and 40 parts by weight of toluene, 4.0 parts by weight of 1-n-octadecyl-3,3-dimethylspiro[indoline-2,3'-(3H)-pyrido(3,4-f)(1,4)-benzooxazine] were dissolved along with 60 parts by weight of an epoxy resin precursor, "EPONIX #1100 CLEAR" (trade name; product of Dai Nippon Toryo Co., Ltd.) to obtain a coating formulation.

The coating formulation was applied by the dipping technique on the surface of a slide glass. The solvent was evaporated at 40° C. until the coated surface became tack-free. Thereafter, the coating formulation was hardened at 80° C. for 16 hours, thereby forming a photochromic film of 10 μm thick.

The thus-formed film was somewhat greenish. When the film was exposed to ultraviolet light, it developed a color. Its light transmittance at room temperature at the wavelength of 612 nm was widely lowered from 90% before the exposure of the ultraviolet light to 48% upon the 5 minutes exposure of the ultraviolet light. When it was placed in a dark place thereafter, the light transmittance returned to its original state.

Furthermore, the film was subjected to an accelerated deterioration treatment in the same manner as in Example 5, and then exposed to ultraviolet light in the same manner as described above so as to measure its light transmittance at the wavelength of 612 nm. The light transmittance was widely lowered from 89% before the exposure of the ultraviolet light to 60% upon the 5 minutes exposure of the ultraviolet light.

EXAMPLE 11

Synthesis Example

Synthesis of
1-(2-ethylhexyl)-3,3-dimethylspiro[indoline-2,3'-(3H)-pyrido(3,4-f)(1,4)benzooxazine]

Dissolved in 200 ml of toluene were 8.14 g of 1-(2-ethylhexyl)-3,3-dimethyl-2-dimethyl-2-methyleneindoline and 5.22 g of 8-nitroso-7-isoquinolinol. The resultant solution was refluxed and reacted for 8 hours in a nitrogen gas atmosphere.

After the reaction, the solvent was concentrated to obtain a viscous liquid having a blackish brown color. The component soluble in hexane was extracted from the thus-obtained liquid. The extractant was concentrated and was purified by recrystallization from a mixed solvent of acetone and hexane to obtain 1.4 g of pale yellow powder.

This compound was identified as 1-(2-ethylhexyl)-3,3-dimethylspiro[indoline-2,3'-(3H)-pyrido(3,4-f)(1,4)-benzooxazine] by NMR spectra, infrared absorption spectra and CHN elemental analysis.

A result of the elemental analysis was as follows:
C: 78.53 wt. %, H: 7.92 wt. %, N: 9.44 wt. %.
These values almost corresponded to the following calculated values:
C: 78.65 wt. %, H: 7.78 wt. %, N: 9.83 wt. %.
On the other hand, NMR spectra of the compound were found to be 0.6–2.0 ppm (21H), 3.2 ppm (2H), 6.5–10.0 ppm (10H) in deuteriochloroform.

Application Example

A photochromic film having a thickness of 10 μm was formed in exactly the same manner as in Example 10 except that 4.0 parts by weight of 1-(2-ethylhexyl)-3,3-dimethylspiro[indoline-2,3'-(3H)-pyrido(3,4-f)(1,4)-benzooxazine] were used instead of 4.0 parts by weight of 1-n-octadecyl-3,3-dimethylspiro[indoline-2,3'-(3H)-pyrido(3,4-f)(1,4)-benzooxazine].

The thus-formed film was somewhat greenish. When the film was exposed to ultraviolet light, it developed a color. Its light transmittance at room temperature at the wavelength of 612 nm was widely lowered from 91% before the exposure of the ultraviolet light to 51% upon the 5 minutes exposure of the ultraviolet light. When it was placed in a dark place thereafter, the light transmittance returned to its original state.

Furthermore, the film was subjected to an accelerated deterioration treatment in the same manner as in Example 5, and then exposed to ultraviolet light in the same manner as described above so as to measure its light transmittance at the wavelength of 612 nm. The light transmittance was widely lowered from 90% before the exposure of the ultraviolet light to 63% upon the 5 minutes exposure of the ultraviolet light.

EXAMPLE 12

Synthesis Example

Synthesis of a mixture of
1-n-hexyl-3,3,4,5-tetramethylspiro[indoline-2,3'-(3H)-pyrido(3,4-f)(1,4)-benzooxazine] and
1-n-hexyl-3,3,5,6-tetramethylspiro[indoline-2,3'-(3H)-pyrido(3,4-f)(1,4)-benzooxazine]

Dissolved in 300 ml of toluene were 13.57 g of a mixture of 1-n-hexyl-3,3,4,5-tetramethyl-2-methyleneindoline and 1-n-hexyl-3,3,5,6-tetramethyl-2-methyleneindoline and 8.88 g of 8-nitroso-7-isoquinolinol. The resultant solution was refluxed and reacted for 8 hours in a nitrogen gas atmosphere.

After the reaction, the solvent was concentrated to obtain a viscous liquid having a blackish brown color. The component soluble in hexane was extracted from the thus-obtained liquid. The extractant was concentrated and was purified by recrystallization from a mixed solvent of acetone and hexane to obtain 2.8 g of pale yellow powder.

This substance was identified as a mixture of 1-n-hexyl-3,3,4,5-tetramethylspiro[indoline-2,3'-(3H)-pyrido(3,4-f)(1,4)benzooxazine] and 1-n-hexyl-3,3,5,6-tetramethylspiro[indoline-2,3'-(3H)-pyrido(3,4-f)(1,4)-benzooxazine] by NMR spectra, infrared absorption spectra and CHN elemental analysis.

A result of the elemental analysis was as follows:
C: 76.53 wt. %, H: 7.95 wt. %, N: 9.66 wt. %.
These values almost corresponded to the following calculated values:
C: 78.56 wt. %, H: 7.78 wt. %, N: 9.83 wt. %.
On the other hand, NMR spectra of the compound were found to be 0.6–1.9 ppm (17H), 2.3 ppm (6H), 3.2 ppm (2H), 6.5–10.0 ppm (8H) in deuteriochloroform.

Application Example

A photochromic film having a thickness of 10 μm was formed in exactly the same manner as in Example 10 except that 4.0 parts by weight of the mixture of 1-n-hexyl-3,3,4,5-tetramethylspiro[indoline-2,3'-(3H)-pyrido(3,4-f)(1,4)benzooxazine] and 1-n-hexyl-3,3,5,6-tetramethylspiro[indoline-2,3'-(3H)-pyrido(3,4-f)(1,4)-benzooxazine] were used instead of 4.0 parts by weight of 1-n-octadecyl-3,3-dimethylspiro[indoline-2,3'-(3H)-pyrido(3,4-f)(1,4)-benzooxazine], and 0.5 part by weight of 1-{2-[3-(3,5-di-tert-butyl-4-hydroxyphenyl)propionyloxy]ethyl}-4-{3-(3,5-di-tert-butyl-4-hydroxyphenyl)propionyloxy]-2,2,6,6-tetramethylpiperidine ("SANOL LS-2626"; trade name; product of Sankyo Company, Limited) of a hindered amine type light stabilizer was added further to the coating formulation.

The thus-formed film was somewhat greenish. When the film was exposed to ultraviolet light, it developed a color. Its light transmittance at room temperature at the wavelength of 612 nm was widely lowered from 88% before the exposure of the ultraviolet light to 41% upon the 5 minutes exposure of the ultraviolet light. When it was placed in a dark place thereafter, the light transmittance returned to its original state.

Furthermore, the film was subjected to an accelerated deterioration treatment in the same manner as in Example 5, and then exposed to ultraviolet light in the same manner as described above so as to measure its light transmittance at the wavelength of 612 nm. The light transmittance was widely lowered from 90% before the exposure of the ultraviolet light to 58% upon the 5 minutes exposure of the ultraviolet light.

Having now fully described the invention, it will be apparent to one of ordinary skill in the art that many changes and modifications can be made thereto without departing from the spirit or scope of the invention as set forth herein.

We claim:

1. A photochromic compound represented by the following general formula (I):

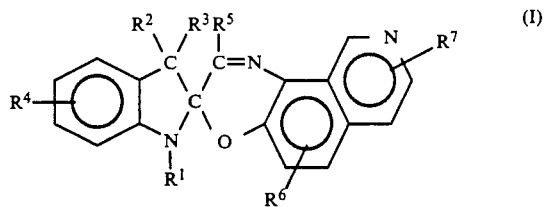

wherein $R^1$ is a linear or branched alkyl group, having 7-25 carbon atoms, allyl or alkoxyalkyl group, or an aralkyl or aryloxyalkyl group, $R^2$ and $R^3$ individually denote an alkyl group, $R^4$, $R^5$, $R^6$ and $R^7$ stand individually for a hydrogen or halogen atom, or an alkyl, alkoxy, hydroxy, alkoxyalkyl, or amino group.

2. The photochromic compound of claim 1, wherein $R^1$ is a linear or branched alkyl group having 7-25 carbon atoms, an allyl group, an alkoxyalkyl group, an arylalkyl group or an aryloxyalkyl group, $R^2$ and $R^3$ individually denote an alkyl group, $R^4$, $R^5$, $R^6$ and $R^7$ stand individually for a hydrogen or halogen atom, or an alkyl, alkoxy, hydroxy, alkoxyalkyl, or amino group.

3. The photochromic compound of claim 1, wherein $R^1$ is a linear or branched alkyl group having 7-25 carbon atoms, an alkoxyalkyl group or an aryloxyalkyl group, $R^2$ and $R^3$ individually denote an alkyl group, $R^4$, $R^5$, $R^6$ and $R^7$ stand individually for a hydrogen or halogen or an alkyl, alkoxy, hydroxy, alkoxyalkyl, or amino group.

4. A photochromic compound represented by the following formula (I):

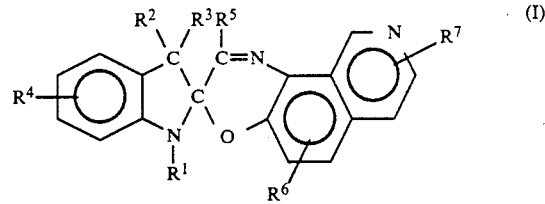

wherein $R^1$ is an allyl or alkoxyalkyl group, or aralkyl or aryloxyalkyl group, $R^2$ and $R^3$ individually denote an alkyl group, $R^4$, $R^5$, $R^6$ and $R^7$ stand individually for a hydrogen or halogen atom, or an alkyl, alkoxy, hydroxy, alkoxyalkyl, or amino group.

* * * * *